US006337297B1

(12) United States Patent
Mimura et al.

(10) Patent No.: US 6,337,297 B1
(45) Date of Patent: Jan. 8, 2002

(54) CATALYST FOR TRIMERIZATION OF ETHYLENE AND PROCESS FOR TRIMERIZING ETHYLENE USING THE CATALYST

(75) Inventors: Hideyuki Mimura, Shinnanyo; Motohiro Oguri, Yokkaichi; Toshihide Yamamoto, Yokkaichi; Hideyuki Murakita, Yokkaichi; Hisanori Okada, Yokkaichi; Toru Yoshida, Kuwana, all of (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 09/457,522

(22) Filed: Dec. 9, 1999

(30) Foreign Application Priority Data

Oct. 12, 1998 (JP) .................................................. 10-351134
Nov. 12, 1998 (JP) .................................................. 10-352540

(51) Int. Cl.$^7$ .............................. B01J 31/00; B01J 37/00; C08F 4/02; C08F 4/60; C07C 2/58
(52) U.S. Cl. .......................... 502/117; 585/721; 585/722; 585/726; 585/727; 585/730; 585/732; 502/123; 502/167; 502/168; 502/169; 502/170
(58) Field of Search ............................ 502/117; 585/721, 585/722, 726, 727, 730, 732

(56) References Cited

U.S. PATENT DOCUMENTS

| 3,033,878 A | * | 5/1962 | Zeiss et al. ................... 502/117 |
| 3,149,080 A | * | 9/1964 | Gluesenkamp et al. ...... 502/117 |
| 3,223,688 A | * | 12/1965 | Badin ........................... 502/117 |
| 3,316,235 A | * | 4/1967 | Yazima et al. ................ 502/117 |
| 5,780,698 A |   | 7/1998 | Baralt et al. |
| 5,891,816 A | * | 4/1999 | Wang et al. ................... 502/117 |
| 6,180,552 B1 | * | 1/2001 | Hlatky ........................... 502/117 |
| 6,197,901 B1 | * | 3/2001 | Rohde et al. ................. 502/117 |

FOREIGN PATENT DOCUMENTS

| JP | 10-7712 | 1/1998 |
| JP | 10-71335 | 3/1998 |
| JP | 10-231317 | 9/1998 |
| JP | 10-287690 | 10/1998 |
| JP | 11-60627 | 3/1999 |

* cited by examiner

Primary Examiner—Mark L. Bell
Assistant Examiner—J. Pasteczyk
(74) Attorney, Agent, or Firm—Oblon, Spivak, McClelland, Maier & Neustadt, P.C.

(57) ABSTRACT

A catalyst for trimerization of ethylene is disclosed which comprises (a) a chromium complex having a neutral multidentate ligand having a tripod structure, represented by the formula, $ACrJ_nQ_{3-n}$ wherein A is a neutral multidentate ligand having a tripod structure, J is a carbonyl ligand or halogen, n is an integer of 0–3, and Q is at least one member selected from hydrogen, a $C_1$–$C_{10}$ hydrocarbon group, a $C_1$–$C_{10}$ carboxylate group, a $C_3$–$C_{10}$ diketonato group, an amide group, an imide group, an $C_1$–$C_{10}$ alkoxide group, a $C_1$–$C_{10}$ thioalkoxide group, an $C_6$–$C_{15}$ arene ligand, an $C_2$–$C_{10}$ alkene ligand, an $C_2$–$C_{15}$ alkyne ligand, an amine ligand, an imine ligand, an isonitrile ligand, a phosphine ligand, a phosphine oxide ligand, a phosphite ligand, an ether ligand, a sulfide ligand, a sulfone ligand and a sulfoxide ligand, and (b) a metal alkyl compound. The catalyst optionally further comprises (c) at least one compound selected from aromatic tertiary amine compounds, except for an imine, and nitrogen-containing heterocyclic compounds, and (d) a radical anion compound.

13 Claims, No Drawings

CATALYST FOR TRIMERIZATION OF ETHYLENE AND PROCESS FOR TRIMERIZING ETHYLENE USING THE CATALYST

BACKGROUND OF THE INVENTION (1) Field of the Invention

This invention relates to a catalyst for trimerization of ethylene and a process for trimerizing ethylene using the catalyst. More specifically, it relates to a catalyst exhibiting an enhanced activity for trimerization of ethylene to produce 1-hexene, which is used as a comonomer for the production of linear low-density polyethylene (LLDPE), and further to a process for trimerizing ethylene by which 1-hexene can be produced effectively and highly selectively.

(2) Related Art

It is known to use a chromium compound as a catalyst for trimerization of ethylene to give 1-hexene. For example, a catalyst system comprising a chromium compound, polyhydrocarbylaluminum oxide and a donor ligand is described in Japanese Unexamined Patent Publication No. (hereinafter abbreviated to "JP-A") S62-265237. A catalyst system comprising a chromium compound, a pyrrole-containing compound, an alkyl metal compound and a halide is described in JP-A H6-239920. A catalyst system comprising a chromium compound, an alkyl metal compound, and an acid amide or imide compound is described in JP-A HB-59732. A catalyst comprising (i) a complex of chromium salt with a multidentate ligand selected from phosphine, arsine and stibine, and (ii) aluminoxane is described in JP-A H6-298673. A catalyst comprising (i) a chromium-chlorine complex or alkyl chromium complex having a specific nitrogen ligand and (ii) an aluminum compound is described in JP-A H10-7712. A catalyst comprising (i) a chromium complex having a cyclic polyamine or hydro-tris(pyrazolyl)borate ligand and (ii) an alkyl aluminum compound is described in JP-A HIO-231317.

However, these chromium catalysts have problems as explained below.

When the catalyst of JP-A S62-265237 is used for trimerization of ethylene, a salient amount of polyethylene is produced in addition to 1-hexene. Further, polyhydrocarbylaluminum oxide (i.e., aluminoxane), which is one ingredient of the catalyst, is a polymer prepared by reacting an alkyl aluminum with water, and therefore, it is difficult to prepare aluminoxane having a predetermined quality, and this leads to reduction of reproducibility of trimerization reaction of ethylene.

When the catalyst of JP-A H6-239920 is used, the amount of polyethylene produced can be reduced. However, a pyrrole-containing compound, which is one ingredient of the catalyst, is extremely unstable to air, and readily deteriorated and colored. Thus, a pyrrole-containing compound is troublesome to handle, and a treating process or apparatus for removing a coloring matter from the catalyst or purifying the catalyst is needed.

As for the catalyst of JP-A H8-59732, among the acid amide or imide compounds, which are one ingredient of the catalyst, maleimide is optimum for the catalytic activity for trimerization of ethylene. However, maleimide has problems such that it has a poor solubility in an organic solvent and the catalyst is troublesome to prepare, and further that it is not readily commercially available and is expensive.

The catalyst of JP-A H6-298673 has a problem such that alminoxane used as one ingredient of the catalyst is difficult to synthesize with a good reproducibility. The catalyst of JP-A H10-7712 has a poor activity for trimerization of ethylene. The catalyst of JP-A H10-231317 has problems such that polyethylene is undesirably produced in an amount larger than that of 1-hexene, and that the selectivity to 1-hexene among oligomers is low.

SUMMARY OF THE INVENTION

In view of the foregoing, a primary object of the present invention is to provide a catalyst having good handling characteristics and exhibiting an enhanced activity for trimerization of ethylene to produce 1-hexene, which is used as a comonomer for the production of linear low-density polyethylene (LLDPE).

Another object of the present invention is to provide a process for trimerizing ethylene by which 1-hexene can be produced effectively and highly selectively.

In one aspect of the present invention, there is provided a catalyst for trimerization of ethylene which comprises:

(a) a chromium complex having a neutral multidentate ligand having a tripod structure, represented by the following formula (1):

$$ACrJ_nQ_{3-n} \tag{1}$$

wherein A is a neutral multidentate ligand having a tripod structure, J is a carbonyl ligand or a halogen atom, n is an integer of 0 to 3, and Q is at least one member selected from the group consisting of a hydrogen atom, a hydrocarbon group having 1 to 10 carbon atoms, a carboxylate group having 1 to 10 carbon atoms, a diketonato group having 3 to 10 carbon atoms, an amide group, an imide group, an alkoxide group having 1 to 10 carbon atoms, a thioalkoxide group having 1 to 10 carbon atoms, an arene ligand having 6 to 15 carbon atoms, an alkene ligand having 2 to 10 carbon atoms, an alkyne ligand having 2 to 15 carbon atoms, an amine ligand, an imine ligand, a nitrile ligand, an isonitrile ligand, a phosphine ligand, a phosphine oxide ligand, a phosphite ligand, an ether ligand, a sulfide ligand, a sulfone ligand and a sulfoxide ligand, and (b) a metal alkyl compound.

Preferably the catalyst further comprises (c) at least one compound selected from aromatic tertiary amine compounds, except for an imine, and nitrogen-containing heterocyclic compounds, and/or (d) a radical anion compound.

In another aspect of the present invention, there is provided a process for trimerizing ethylene, characterized in that ethylene is trimerized in the presence of the above-mentioned catalyst.

DESCRIPTION OF THE PREFERRED EMBODIMENTS

Catalyst for Trimerization of Ethylene

The catalyst of the invention comprises a chromium complex having a neutral multidentate ligand having a tripod structure, represented by the above formula (1) as one indispensable ingredient. The neutral multidentate ligand having a tripod structure coordinated in the chromium complex is not particularly limited, and includes, for example, those which are represented by the following formulae (2) and (3).

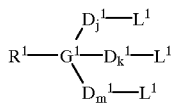

(2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, $G^1$ represents a carbon or silicon atom, and $R^1$ represents a hydrogen atom, an alkyl group having 1 to 10 carbon atoms or an aryl group having 6 to 10 carbon atoms.

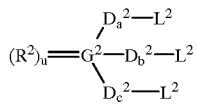

(3)

wherein a, b and c independently represent an integer of 0 to 6, u represents an integer of 0 or 1, each $D^2$ independently represents a divalent hydrocarbon group which may have a substituent, each $L^2$ independently represents a substituent containing an element of group 14, 15, 16 or 17 of the periodic table, $G^2$ represents a nitrogen or phosphorus atom, and $R^2$ represents an oxygen or sulfur atom.

The divalent hydrocarbon groups $D^1$ in formula (2) and $D^2$ in formula (3) are not particularly limited, and include, for example, alkylene, cycloalkylene, phenylene, tolylene and xylylene groups. $D^1$ and $D^2$ may have a substituent, for example, an alkyl group such as methyl or ethyl, and an alkoxy group such as methoxy and ethoxy.

The substituents $L^1$ in formula (2) and $L^2$ in formula (3), which contain an element of group 14, 15, 16 or 17 of the periodic table, are not particularly limited. As specific examples of the substituents $L^1$ and $L^2$, there can be mentioned alkoxy groups such as methoxy, ethoxy, propoxy and butoxy; aryloxy groups such as phenoxy and 2,6-dimethylphenoxy; alkylthio groups such as methylthio, ethylthio, propylthio and butylthio; arylthio groups such as phenylthio and tolylthio; dialkylamino groups such as dimethylamino, diethylamino and bis(trimethylsilyl)amino; diarylamino groups such as diphenylamino; alkylarylamino groups such as methylphenylamino; dialkylphosphino groups such as dimethylphosphino and diethylphosphino; diarylphosphino groups such as diphenylphosphino and ditolylphosphino; and alkylarylphosphino groups such as methylphenylphosphino.

The substituents $L^1$ and $L^2$ further include heterocyclic groups containing an element of group 14, 15, 16 or 17 of the periodic table, such as furyl, benzofuryl, thienyl, benzothienyl, pyrazolyl, triazolyl, tetrazolyl, pyridyl, imidazolyl, benzoimidazolyl, indazolyl, quinolyl, isoquinolyl, oxazolyl and thiazol. These heterocyclic groups may have a substituent on the ring thereof, such as, for example, methyl, ethyl, propyl, butyl, octyl and phenyl.

$R^1$ in formula (2) is not particularly limited, and include, for example, a hydrogen atom, alkyl groups having 1 to 10 carbon atoms such as methyl, ethyl, propyl, butyl, benzyl, hydroxymethyl, cyanoethyl, allyl and trifluoropropyl, and aryl groups having 6 to 10 carbon atoms such as phenyl, p-methylphenyl and p-chlorophenyl.

The neutral multidentate ligand having a tripod structure, represented by formula (2) or (3), which has a substituent containing an element of group 14, 15, 16 or 17 of the periodic table, is not particularly limited. As specific examples of the neutral multidentate ligand, there can be mentioned oxygen-containing tridentate ligands such as tris(methoxymethyl)methane, 1,1,1-tris(methoxymethyl)ethane, 1,1,1-tris(methoxymethyl)propane, 1,1,1-tris(methoxymethyl)butane, 1,1,1-tris(ethoxymethyl)ethane, 1,1,1-tris(propoxymethyl)ethane, 1,1,1-tris(butoxymethyl)ethane and 1,1,1-tris(phenoxymethyl)ethane; sulfur-containing tridentate ligands such as 1,1,1-tris(methylthiomethyl)ethane, 1,1,1-tris(butylthiomethyl)ethane and 1,1,1-tris(phenylthiomethyl)ethane; nitrogen-containing tridentate ligands such as 1,1,1-tris(dimethylaminomethyl)ethane and 1,1,1-tris(diphenylaminomethyl)ethane; and phosphorus-containing tridentate ligands such as 1,1,1-tris(diphenylphosphinomethyl)ethane, 1,1,1-tris(dimethylphosphinomethyl)ethane and 1,1,1-tris(diethylphosphinomethyl)ethane.

As specific examples of the neutral multidentate ligand having a tripod structure, represented by formula (2) or (3), which has a heterocyclic substituent containing an element of group 14, 15, 16 or 17 of the periodic table, there can be mentioned oxygen-containing tridentate ligands such as trifurylmethane, tris(5-methyl-2-furyl)methane, tris(5-ethyl-2-furyl)methane, tris(5-butyl-2-furyl)methane, 1,1,1-trifurylethane, trifurylamine, trifurylphosphine and trifurylphosphine oxide; sulfur-containing tridentate ligands such as tris(thienyl)methane; and nitrogen-containing tridentate ligands such as tris(pyrazolyl)methane, tris(3,5-dimethyl-1-pyrazolyl)methane, tris(3,5-diisopropyl-1-pyrazolyl)methane, tris(3,5-diphenyl-1-pyrazolyl)methane, 1,1,1-tris(3,5-dimethyl-1-pyrazolyl)ethane, 1,1,1-tris(3,5-dimethyl-1-pyrazolyl)-propane, 1,1,1-tris(3,5-dimethyl-1-pyrazolyl)butane, tris(2-pyridyl)methane, tris(6-methyl-2-pyridyl)methane, tris(2-pyridyl)amine, tris(2-pyridyl)phosphine, tris(2-pyridyl)phosphine oxide, tris(2-pyridyl)hydroxymethane and tris(1-imidazolyl)methane.

As specific examples of B in formula (1), there can be mentioned hydrocarbon groups having 1 to 10 carbon atoms such as methyl, ethyl, propyl, butyl, cyclohexyl, benzyl and phenyl; carboxylate groups having 1 to 10 carbon atoms such as acetate, naphthenate and 2-ethylhexanoate; diketonato groups having 3 to 10 carbon atoms such as acetylacetonato; arene ligands having 6 to 15 carbon atoms such as benzene, toluene, xylene, trimethylbenzene, hexamethylbenzene and naphthalene; alkene ligands having 2 to 10 carbon atoms such as ethylene, propylene, butene, hexene and decene; alkyne ligands having 2 to 15 carbon atoms such as acetylene, phenylacetylene and diphenylacetylene; amine ligands such as triethylamine, tributylamine, N,N- dimethylaniline, N,N-diethylaniline, N,N-dibutylaniline, diphenylmethylamine, triphenylamine, pyridine and quinoline; imine ligands such as benzophenone imine and methyl-ethyl-ketone imine; amide groups such as dimethylamide, diethylamide, diisopropylamide, dioctylamide, didecylamide, didodecylamide, bis(trimethylsilyl)amide, pyrrolido, indole, maleimide, phthalimide, diphenylamide, N-methylanilide and anilide; alkoxide groups having 1 to 10 carbon atoms such as methoxide, ethoxide, propoxide, butoxide and phenoxide; thioalkoxide groups having 1 to 10 carbon atoms such as thiomethoxide, thioethoxide, thiopropoxide, thiobutoxide and thiophenoxide; imide groups such as benzophenone imide; nitrile groups such as acetonitrile and benzonitrile; isonitrile groups such as t-butylisonitrile and phenylisonitrile; phosphine ligands such as triphenylphosphine, tritolylphosphine, tricyclohexylphosphine and tributylphosphine; phosphite ligands such as triphenyl phosphite, tritolyl phosphite, tributyl phosphite and triethyl phosphite; phosphine oxide ligands such as tributylphosphine oxide and triphenylphosphine oxide; ether ligands such as dimethyl ether, diethyl ether and tetrahydrofuran; sulfide ligands such as ethylsulfide and butylsulfide; sulfone ligands such as dimethylsulfone and dibutylsulfone; and sulfoxide ligands such as dimethylsulfoxide and dibutylsulfoxide.

The halogen atom J in formula (1) is not particularly limited, and includes, for example, fluorine, chlorine, bromine and iodine atoms.

As specific examples of the chromium complex of formula (1), there can be mentioned 1,1,1-tris(methoxymethyl)ethanechromium tricarbonyl(0), trifurylmethanechromium tricarbonyl(0), tris(5-methyl-2-furyl)methanechromium tricarbonyl(0), tris(5-butyl-2-furyl)methanechromium tricarbonyl(0), trifurylaminechromium tricarbonyl(0), trifurylphosphinechromium tricarbonyl(0), trifurylphosphineoxidechromium tricarbonyl(0), 1,1,1-tris(methylthiomethyl)ethanechromium tricarbonyl(0), tris(thienyl)methanechromium tricarbonyl(0), 1,1,1-tris(dimethylaminomethyl)ethanechromium tricarbonyl(0), tris(pyrazolyl)methanechromium tricarbonyl(0), tris(3,5-dimethyl-1-pyrazolyl)methanechromium tricarbonyl(0), tris(3,5-dimethyl-1-pyrazolyl)methanechromium (ethylene)dicarbonyl(0), tris(3,5-dimethyl-1-pyrazolyl)methanechromium (phenylacetylene)dicarbonyl(0), tris(3,5-dimethyl-1-pyrazolyl)methanechromium (dimethylaniline)dicarbonyl(0), tris(3,5-dimethyl-1-pyrazolyl)methanechromium (benzophenoneimine)dicarbonyl(0), tris(3,5-dimethyl-1-pyrazolyl)methanechromium (acetonitrile)dicarbonyl(0), tris(3,5-dimethyl-1-pyrazolyl)methanechromium (t-butylisonitrile)dicarbonyl(0), tris(3,5-dimethyl-1-pyrazolyl)methanechromium (tributylphosphine)dicarbonyl(0), tris(3,5-dimethyl-1-pyrazolyl)methanechromium (tributylphosphineoxide)dicarbonyl(0), tris(3,5-dimethyl-1-pyrazolyl)methanechromium (triphenylphosphite)-dicarbonyl(0), tris(3,5-dimethyl-1-pyrazolyl)methanechromium (tetrahydrofuran)dicarbonyl(0), tris(3,5-dimethyl-1-pyrazolyl)methanechromium (dimethylsulfone)dicarbonyl(0), tris(3,5-dimethyl-1-pyrazolyl)methanechromium (dimethylsulfoxide)dicarbonyl(0), tris(3,5-dimethyl-1-pyrazolyl)methanechromium (dibutylsulfide)dicarbonyl(0), tris(3,5-diisopropyl-1-pyrazolyl)methanechromium tricarbonyl(0), tris(3,5-diphenyl-1-pyrazolyl)methanechromium tricarbonyl(0), 1,1,1-tris(3,5-dimethyl-1-pyrazolyl)ethanechromium tricarbonyl(0), 1,1,1-tris(3,5-dimethyl-1-pyrazolyl)propanechromium tricarbonyl (0), 1,1,1-tris(3,5-dimethyl-1-pyrazolyl)butanechromium tricarbonyl(0), tris(2-pyridyl)methanechromium tricarbonyl (0), tris(6-methyl-2-pyridyl)methanechromium tricarbonyl (0), tris(2-pyridyl)aminechromium tricarbonyl(0), tris(2-pyridyl)phosphinechromium tricarbonyl(0), tris(2-pyridyl)phosphine-oxide-chromium tricarbonyl(0), tris(1-imidazolyl)methanechromium tricarbonyl(0), 1,1,1-tris(diphenylphosphinomethyl)ethanechromium tricarbonyl(0), 1,1,1-tris(dimethylphosphinomethyl)ethanechromium tricarbonyl(0), 1,1,1-tris(diethylphosphinomethyl)ethanechromium tricarbonyl(0), tris(methoxymethyl)methanechromium tris(diisopropylamide)(III), tris(methoxymethyl)methanechromium tris(dizenzylamide)(III), 1,1,1-tris(ethoxymethyl)ethanechromium tris(diisopropylamide)(III), 1,1,1-tris(butoxymethyl)ethanechromium tris(diisopropylamide) (III), 1,1,1-tris(phenoxymethyl)ethanechromium tris(diisopropylamide)(III), triphenylmethanechromiumn tris(diisopropylamide)(III), 1,1,1-tris(methylthiomethyl)ethanechromium tris(diisopropylamide)(III), 1,1,1-tris(dimethylaminomethyl)ethanechromium tris(diisopropylamide)(III), tris(pyrazolyl)methanechromium tris(diisopropylamide)(III), tris(3,5-dimethyl-1-pyrazolyl)methanechromium tris(diethylamide)(III), tris(3,5-dimethyl-1-pyrazolyl)methanechromium tris(diisopropylamide)(III), tris(3,5-dimethyl-1-pyrazolyl)methanechromium tris(dibenzylamide)(III), tris(3,5-dimethyl-1-pyrazolyl)methanechromium tris(diphenylamide)(III), tris(3,5-dimethyl-1-pyrazolyl)methanechromium tris[bis(trimethylsilyl)amide](III), tris(3,5-dimethyl-1-pyrazolyl)methanechromium triethoxide(III), tris(3,5-dimethyl-1-pyrazolyl)methanechromium tributoxide(III), tris(3,5-dimethyl-1-pyrazolyl)methanechromium thiobutoxide(III), tris(3,5-dimethyl-1-pyrazolyl)methanechromium bis(diisopropylamide)(III), tris(3,5-diphenyl-1-pyrazolyl)methanechromium tris(diisopropylamide)(III), tris(2-pyridyl)methanechromium tris(diisopropylamide)(III), tris(6-methyl-2-pyridyl)methanechromium tris(diisopropylamide)(III), tris(2-pyridyl)aminechromium tris(diisopropylamide)(III), tris(1-imidazolyl)methanechromium tris(diisopropylamide)(III), 1,1,1-tris(dimethylphosphinomethyl)ethanechromium tris(diisopropylamide)(III), 1,1,1-tris(diphenylphosphinomethyl)ethanechromium tris(diisopropylamide)(III), 1,1,1-tris(diethylphosphinomethyl)ethanechromium tris(diisopropylamide)(III), tris(methoxymethyl)methanechromium trichloride(III), 1,1,1-tris(methoxymethyl)ethanechromium trichloride(III), 1,1,1-tris(methoxymethyl)ethane-tris(diisopropylamide)chromium(III), 1,1,1-tris(methoxymethyl)ethane-tris(dimethylamide)chromium(III), 1,1,1-tris(methoxymethyl)ethane-tris[bis(trimethylsilyl)amide]chromium(III), 1,1,1-tris(methoxymethyl)ethanechromium triethoxide(III), 1,1,1-tris(methoxymethyl)ethanechromium trithiobutoxide(III), 1,1,1-tris(ethoxymethyl)ethanechromium trichloride(III), 1,1,1-tris(butoxymethyl)ethanechromium trichloride(III), 1,1,1-tris(phenoxymethyl)ethanechromium trichloride(III), tris(3, 5-dimethyl-1-pyrazolyl)methanechromium trichloride(III), tris(3,5-dimethyl-1-pyrazolyl)methane-tris(diethylamide) chromium(III), tris(3,5-dimethyl-1-pyrazolyl)methane-tris (diisopropylamide)chromium(III), tris(3,5-dimethyl-1-pyrazolyl)methane-tris[bis(trimethylsilyl)amide]chromium (III), tris(3,5-dimethyl-1-pyrazolyl)methane-tris (benzophenoneimide)chromium(III), tris(3,5-dimethyl-l-pyrazolyl)methanechromium triethoixide(III), tris(3,5-dimethyl-1-pyrazolyl)methanechromium trithiobutoxide (III), 1,1,1-tris(diphenylphosphinomethyl)ethanechromium trichloride(III), 1,1,1-tris(diethylphosphinomethyl) ethanechromium trichloride(III), and 1,1,1-tris (diethylphosphinomethyl)ethane-tris(diisopropylamide) chromium(III).

Among the neutral multidentate ligands having a tripod structure, represented by formula (1), tridentate ligands having a nitrogen-containing heterocyclic group are preferable in view of the selectivity to 1-hexene and the catalyst activity. Tris(3,5-dimethyl-1-pyrazolyl)methane is especially preferable.

As preferable examples of the chromium carbonyl complexes having a neutral multidentate ligand having a tripod structure, there can be mentioned tris(3,5-dimethyl-1-pyrazolyl)methanechromium tricarbonyl(0), tris(3,5-dimethyl-1-pyrazolyl)methanechromium trichloride(III), 1,1,1-tris(diphenylphosphinomethyl)ethanechromium tricarbonyl(0), tris(3,5-dimethyl-1-pyrazolyl) methanechromium tris(diethylamide)(III), tris(3,5-dimethyl-1-pyrazolyl)methanechromium tris (diisopropylamide)(III), tris(3,5-dimethyl-l-pyrazolyl) methanechromium tris(diphenylamide)(III), tris(3,5-dimethyl-1-pyrazolyl)methanechromium tris[bis (trimethylsilyl)amide](III), and 1,1,1-tris-(methoxymethyl) ethanechromium tricarbonyl(0).

The process for synthesizing the chromium carbonyl complex having a neutral multidentate ligand having a tripod structure is not particularly limited. For example, the chromium carbonyl complex can be synthesized from a neutral multidentate ligand having a tripod structure and a chromium carbonyl compound by known complex synthesizing processes (for example, by a process described in J. Amer. Chem. Soc., 92, 5118.

The chromium carbonyl compound used as a raw material is not particularly limited, and includes, for example, chromium hexacarbonyl(0), pentacarbonyl(triphenylphosphine) chromium(0), tetracarbonylbis(ethylene)chromium(0), tricarbonyl(benzene)chromium(0), tricarbonyl(toluene) chromium(0), tricarbonyl(trimethylbenzene)chromium(0), tricarbonyl(hexamethylbenzene)chromium(0), tricarbonyl (naphthalene)chromium(0), tricarbonyl(cycloheptatriene) chromium(0), tricarbonyl tris(acetonitrile)chromium(0), tricarbonyl tris(triphenylphosphite)chromium(0) (ethylene) dicarbonyl (trimethylbenzene)chromium(0), cyclohexylisonitriledicarbonyl (trimethylbenzene) chromium(0), tributylphosphinedicarbonyl (trimethylbenzene)chromium(0), tricarbonyl (cyclopentadienyl)chromium(I) dimer, and hydridotricarbonyl (cyclopentadienyl)chromium(II). Of these, chromium hexacarbonyl(0) and tricarbonyl(trimethylbenzene) chromium(0) are preferable in view of handling properties and commercial availability.

The process for synthesizing the chromium halogen complex and other chromium complexes, which have a neutral multidentate ligand having a tripod structure, is not particularly limited. For example, the chromium halogen complex can be synthesized from a neutral multidentate ligand having a tripod structure and a chromium compound by known complex synthesizing processes.

The chromium compounds used as a raw material for the synthesis of the chromium halogen complex and other chromium complexes are not particularly limited, and include, for example, chromium halides such as chromium chloride(III), chromium chloride(II), chromium bromide (III), chromium bromide(II), chromium iodide(III), chromium iodide(II), chromium fluoride(III), chromium fluoride (II); chromium chloride complexes such as tris (tetrahydrofuran)chromium trichloride(III), tris(1,4-dioxane)chromiumtrichloride(III), tris(diethyl ether)-chromium trichloride(III), tris(pyridine)chromium trichloride(III), tris(acetonitrile)chromium trichloride(III); chromium amide complexes such as tris(tetrahydrofuran) chromium tris(diethylamide)(III), tris(tetrahydrofuran) chromium tris(diisopropylamide)(III), tris(tetrahydrofuran) chromium tris(diphenylamide)(III), and tris (tetrahydrofuran)chromium tris[bis(trimethylsilyl)amide] (III); chromium carboxylate complexes such as chromium tris(2-ethyl hexanoate)(III) and chromium tris(acetate)(III); chromium diketonato complexes such as chromium acetylacetonato(III); chromium alkoxide complexes such as chromium(IV) t-butoxide and tris(tetrahydrofuran) chromium triethoxide(III); and chromium thioalkoxide complexes such as chromium(IV) thiobutoxide and tris (tetrahydrofuran)chromium trithioethoxide(III).

The concentration of chromium metal in a reaction solution for synthesis of the chromium complex is not particularly limited. The solvent used for the chromium complex synthesis is not particularly limited, and usually organic solvents are used. As specific examples of the organic solvent, there can be mentioned aliphatic hydrocarbons such as pentane, hexane, heptane, octane, nonane, decane, cyclohexane and decalin; aromatic hydrocarbons such as benzene, toluene, xylene, cumene and trimethylbenzene; ethers such as diethyl ether and tetrahydrofuran; and halogenated hydrocarbons such as methylene chloride, chloroform and carbon tetrachloride. Of these, aliphatic hydrocarbons and aromatic hydrocarbons are preferable in view of handling properties. Decalin, trimethylbenzene and toluene are especially preferable. These organic solvents may be used either alone or in combination.

The synthesis of the chromium complex is usually carried out at a temperature in the range of −80° C. to the boiling point of solvent used, preferably in the range of 0 to 200° C. A temperature higher than the boiling point of solvent may also be employed provided that the reaction is conducted under pressure. The reaction time is not particularly limited and is usually in the range of 1 minute to 48 hours, preferably 5 minutes to 24 hours. The operation for the chromium complex synthesis is preferably carried out under conditions such that the reactants are not in contact with air and moisture. The raw materials used are preferably preliminarily dried.

Another process may be employed wherein the chromium complex having a neutral multidentate ligand having a tripod structure is synthesized by allowing a chromium halogen complex having a neutral multidentate ligand having a tripod structure to react with a metal alkylamide, a metal alkoxide or a metal thioalkoxide in a solvent.

The chromium halogen complex having a neutral multidentate ligand having a tripod structure used is not particularly limited, and includes, for example, 1,1,1-tris(methoxymethyl)ethanechromium trichloride(III), 1,1,1-tris(methoxymethyl)propanechromium trichloride(III), 1,1,1-tris(ethoxymethyl)ethanechromium trichloride(III), 1,1,1-tris(butoxymethyl)ethanechromium trichloride(III), 1,1,1-tris(methylthiomethyl)ethanechromium trichloride(III), 1,1,1-tris(dimethylaminomethyl)ethanechromium trichloride(III), 1,1,1-tris(diphenylphosphinomethyl)ethanechromium trichloride(III), trifurylmethanechromium trichloride(III), tris(5-methyl-2-furyl)methanechromium trichloride(III), trifurylphosphineoxidechromium trichloride(III), tris(pyrazolyl)methanechromium trichloride(III), tris(3,5-dimethyl-1-pyrazolyl)methanechromium trichloride(III), tris(3,5-diisopropyl-1-pyrazolyl)methanechromium trichloride(III), tris(2-pyridyl)methanechromium trichloride(III), and tris(6-methyl-2-pyridyl)methanechromium trichloride(III).

The metal alkylamide, metal alkoxide and metal thioalkoxide also are not particularly limited, and include, for example, lithium dimethylamide, lithium diethylamide, lithium diisopropylamide, lithium bis(trimethylsilyl)amide, sodium bis(trimethylsilyl)amide, sodium diphenylamide, sodium methoxide, sodium ethoxide, sodium propoxide, sodium phenoxide, sodium thiomethoxide, sodium thioethoxide, sodium thiobutoxide and sodium thiophenoxide.

The thus-produced chromium complex having a neutral multidentate ligand having a tripod structure usually precipitates, and therefore, can be separated from the solvent by filtration. If desired, the separated chromium complex is washed with the same solvent, and then dried. If the produced chromium complex does not precipitate, it can be precipitated by removing the solvent by distillation, adding a poor solvent, or cooling the reaction product mixture.

Among the chromium complexes having a neutral multidentate ligand having a tripod structure, those in which the multidentate ligand is facially coordinated are preferable because production of side-reaction products such as polyethylene is minimized. By the term "facially coordinated" used herein, we mean that the neutral multidentate ligand occupies the three coordinate sites to form an isomer of six-coordinate octahedral complex (Kagaku-sensho: Organic Metal Chemistry, Fundamental and Application, p143, published by Shoukabou, Japan). That is, the three coordinate sites occupied by the multidentate ligand take a cis-form to each other.

The catalyst of the invention comprises a metal alkyl compound as another indispensable ingredient, in addition to the chromium complex of formula (1) having a neutral multidentate ligand having a tripod structure. The alkyl metal compound is not particularly limited, but those which are represented by the following formula (4) are preferable:

$$R_pEX_q \quad (4)$$

wherein p and q are numbers satisfying the formulae: $0<p\leq 3$ and $0<q\leq 3$, provided that (p+q) is in the range of 1 to 3, E represents lithium, magnesium, zinc, boron or aluminum, each R independently represents an alkyl group having 1 to 10 carbon atoms, and each X independently represents a hydrogen atom, an alkoxide group having 1 to 10 carbon atoms, an aryl group having 6 to 10 carbon atoms or a halogen atom.

As examples of the alkyl group R having 1 to 10 carbon atoms in formula (4), there can be mentioned methyl, ethyl, propyl, butyl, cyclohexyl and octyl groups. As specific examples of X in formula (4), there can be mentioned alkoxide groups such as methoxide, ethoxide, butoxide and phenoxide, aryl groups such as phenyl, and halogen atoms such as fluorine, chlorine, bromine and iodine.

In formula (4), when E is aluminum, each of p and q is 1.5, the metal alkyl compound is represented by the formula $AlR_{1.5}X_{1.5}$. Theoretically this compound does not exist, but, it is popularly called as a sesqui-compound of $Al_2R_3X_3$ and can be used as the alkyl metal compound in the present invention.

As specific examples of the alkyl metal compound, there can be mentioned methyllithium, ethyllithium, propyllithium, n-butyllithium, s-butyllithium, t-butyllithium, diethylmagnesium, ethylbutylmagnesium, ethylchloromagnesium, ethylbromomagnesium, dimethylzinc, diethylzinc, dibutylzinc, trimethylborane, triethylborane, trimethylaluminum, triethylaluminum, triisobutylaluminum, tri-n-hexylaluminum, tri-n-octylaluminum, tricyclohexylaluminum, dimethylethylaluminum, diethylaluminum hydride, diisobutylaluminum hydride, diethylaluminum ethoxide, diethylaluminum phenoxide, dicyclohexylphenylaluminum, ethylaluminum ethoxychloride, diethylaluminum chloride, diethylaluminum bromide, diisobutylaluminum chloride, dicyclohexylaluminum chloride, methylaluminum sesquichloride, ethylaluminum sesquichloride, butylaluminum sesquichloride, ethylaluminum dichloride and isobutylaluminum dichloride.

Of these, alkyl aluminum compounds are preferable in view of commercial availability and catalytic activity. Triethylaluminum and triisobutylaluminum are especially preferable. These alkyl metal compounds may be used either alone or in combination.

The amount of the alkyl aluminum compound is usually in the range of 0.1 to 10,000 equivalent, preferably 3 to 3,000 equivalent and more preferably 5 to 2,000 equivalent, per mol of the chromium complex.

To enhance the activity of the catalyst of the present invention, aromatic tertiary amine compounds, except for an imine, and/or nitrogen-containing heterocyclic compounds can be used as an additional ingredient of the catalyst.

As specific examples of the aromatic tertiary amine compounds, except for an imine, there can be mentioned N,N-dimethylaniline, N,N-diethylaniline, N,N-diisopropylaniline, N,N-dibutylaniline, N,N-dibenzylaniline, Diphenylmethylamine, Triphenylamine, Tris(p-methylphenyl)amine, Tris(m-methylphenyl)amine, Tris(o-methylphenyl)amine, N,N-dimethyl-o-toluidine, N,N-dimethyl-m-toluidine, N,N-dimethyl-p-toluidine, N,N,2,3-tetramethylaniline, N,N,2,4-tetramethylaniline, N,N,2,5-tetramethylaniline, N,N,2,6-tetramethylaniline, N,N,3,4-tetramethylaniline, N,N,3,5-tetramethylaniline, N,N-2,3,4-pentamethylaniline, N,N,2,3,5-pentamethylaniline, N,N-2, 4,6-pentamethylaniline, N,N-3,4,5-pentamethylaniline, N,N-2,3,4,5,6-heptamethylaniline, N,N-dimethyl-2-ethylaniline, N,N-dimethyl-3-ethylaniline, N,N-dimethyl-4-ethylaniline, N,N-dimethyl-6-ethyl-o-toluidine, N,N-dimethyl-2-isopropylaniline, N,N-dimethyl-4-isopropylaniline, N,N-dimethyl-2-t-butylaniline, N,N-dimethyl-4-s-butylaniline, N,N-dimethyl-4-t-butylaniline, N,N-dimethyl-2,6-diethylaniline, N,N-dimethyl-6-isopropyl-o-toluidine, N,N-dimethyl-2-fluoroaniline, N,N-dimethyl-3-fluoroaniline, N,N-dimethyl-4-fluoroaniline, N,N-dimethyl-2,3-difluoroaniline, N,N-dimethyl-2,4-difluoroaniline, N,N-dimethyl-2,5-difluoroaniline, N,N-dimethyl-2,6-difluoroaniline, N,N-dimethyl-3,4-difluoroaniline, N,N-dimethyl-3,5-difluoroaniline, N,N-dimethyl-2,3,4-trifluoroaniline, N,N-dimethyl-2,3,5-trifluoroaniline, N,N-dimethyl-2,4,6-trifluoroaniline, N,N-dimethyl-3,4,5-trifluoroaniline, N,N-dimethyl-2,3,4,5,6-pentafluoroaniline, N,N-dimethyl-3,5-bis(trifluoromethyl)aniline, N,N-dimethyl-2-chloroaniline, N,N-dimethyl-3-chloroaniline, N,N-dimethyl-4-chloroaniline, N,N-dimethyl-2-bromoaniline, N,N-dimethyl-3-bromoaniline, N,N-dimethyl-4-bromoaniline, N,N-dimethyl-o-anisidine, N,N-dimethyl-m-anisidine, N,N-dimethyl-p-anisidine, N,N-dimethyl-o-phenetidine, N,N-dimethyl-m-phenetidine, N,N-dimethyl-p-phenetidine, N,N-dimethyl-1-aminonaphthalene, N,N-dimethyl-2-aminonaphthalene, N,N-dimethyl-1-aminofluorene, N,N-dimethyl-2-aminofluorene, N,N-dimethyl-3-aminofluorene, N,N-dimethyl-4-aminofluorene, N,N-dimethyl-5-aminoindane, N,N-dimethyl-2-aminobiphenyl, N,N-dimethyl-4-aminobiphenyl and N,N-dimethyl-p-trimethylsilylaniline.

As specific examples of the nitrogen-containing heterocyclic compounds, there can be mentioned pyridine, 2-methylpyridine, 3-methylpyridine, 4-methylpyridine, 2,3-dimethylpyridine, 2,4-dimethylpyridine, 2,5-dimethylpyridine, 2,6-dimethylpyridine, 2,3,4-trimethylpyridine, 2,3,5-trimethylpyridine, 2,4,6-trimethylpyridine, 2-ethylpyridine, 3-ethylpyridine, 4-ethylpyridine, 2-isopropylpyridine, 4-isopropylpyridine, 2-t-butylpyridine, 4-t-butylpyridine, 2,6-diethylpyridine, 2,6-di-n-propylpyridine, 2,6-di-i-propylpyridine, 2,6-diphenylpyridine, 2,6-di-t-butylpyridine, 2-methyl-6-ethylpyridine, 2-methyl-6-isopropylpyridine, 2-fluoropyridine, 3-fluoropyridine, 4-fluoropyridine, 2,3-difluoropyridine, 2,4-difluoropyridine, 2,5-difluoropyridine, 2,6-difluoropyridine, 2,3,4-trifluoropyridine, 2,3,5-trifluoropyridine, 2,4,6-trifluoropyridine, pentafluoropyridine, 2-chloropyridine, 3-chloropyridine, 4-chloropyridine, 2-bromopyridine, 3-bromopyridine, 4-bromopyridine, 2-methoxypyridine, 3-methoxypyridine, 4-methoxypyridine, quinoline, isoquinoline, pyridazine, pyrimidine, pyrazine, cinnoline, phthalazine, quinazoline, quinoxaline and acridine.

Among the aromatic tertiary amine compounds, except for an imine, and the nitrogen-containing heterocyclic compounds, the aromatic tertiary amine compounds, except for an imine, are preferable because of high catalyst activity. N,N-dimethylaniline, diphenylmethylamine and triphenylamine are more preferable. These aromatic tertiary amine compounds and nitrogen-containing heterocyclic compounds may be used either alone or as a mixture of at least two thereof.

The amounts of the aromatic tertiary amine compounds, except for an imine, and the nitrogen-containing heterocyclic compounds are usually in the range of 0.01 to 10,000 equivalent, preferably 0.05 to 3,000 equivalent and more preferably 0.1 to 1,000 equivalent, per mol of the chromium complex. When the amount is smaller than 0.01 equivalent per mol of the chromium compound, the catalyst activity is poor. In contrast, even when the amount exceeds 10,000 equivalent, the catalyst activity is not enhanced nor the catalyst becomes costly.

A radical anion compound can be used as an additional ingredient of the catalyst of the invention. The radical anion compound includes, for example, those which are represented by the following formula (5):

$$(ArY)^-_r (M^2)^{r+} \qquad (5)$$

wherein Ar is an aromatic hydrocarbon or a heteroatom-containing aromatic hydrocarbon having at least one heteroatom on the aromatic ring, which heteroatom is selected from the group consisting of elements of group 15 and 16 of the periodic table, wherein said aromatic hydrocarbon and said heteroatom containing aromatic hydrocarbon may have at least one substituent containing an atom of group 13, 14, 15 or 16 of the periodic table, and two adjacent substituents thereof may form a ring together with the carbon atoms bonded thereto; $M^2$ is a metal selected from the group consisting of alkali metals and alkaline earth metals and r is an integer of 1 when $M^2$ is an alkali metal or an integer of 2 when $M^2$ is an alkaline earth metal.

Preferably, Ar in formula (5) includes aromatic hydrocarbons and heteroatom-containing aromatic hydrocarbons, which are represented by the following formulae (6), (7) and (8).

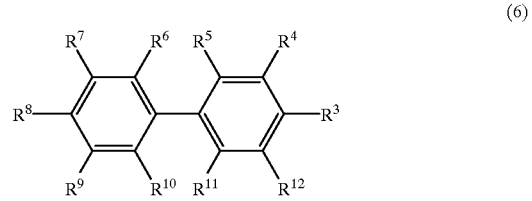

(6)

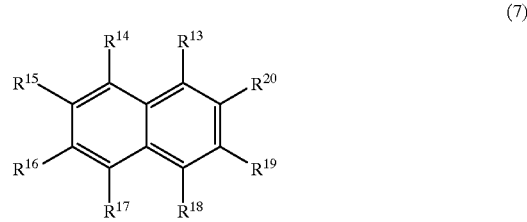

(7)

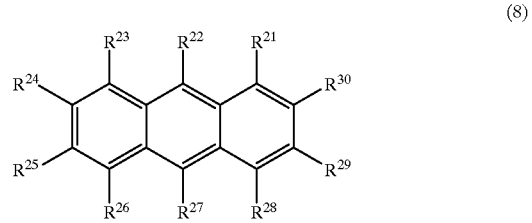

(8)

The hydrocarbons of formula (6) include, for example, biphenyl and its derivatives such as furorene, 4,4'-di(t-butyl)biphenyl and 9H-pyrido[3,4-b]indole. The hydrocarbons of formula (7) include, for example, naphthalene and its derivatives such as 1-(N,N-dimethylamino)naphthalene and quinoline. The hydrocarbons of formula (8) include, for example, anthracene and its derivatives such as 9,10-dimethylanthracene, 3,4-benzopyrene, 2,3-benzofuruorene, 1,2-benzodiphenylene sulfide, acrydine and 3,6-bis(dimethylamino)acrydine.

The metal $M^2$ in formula (5) includes, for example, alkali metals such as lithium, sodium and potassium, and alkaline earth metals such as magnesium.

As specific examples of the radical anion compound of formula (5), there can be mentioned sodium naphthalene, sodium biphenyl, lithium [1-(N,N-dimethylamino)naphthalene], sodium [1-(N,N-dimethylamino)naphthalene], potassium [1-(N,N-dimethylamino)naphthalene], lithium [4,4'-di(t-butyl)biphenyl] and magnesium anthracene. Of these, sodium naphthalene and sodium [1-(N,N-dimethylamino)naphthalene] are preferable in view of good handling properties and high activity.

The amount of the radical anion compound is usually in the range of 0.1 to 10 mols, preferably 1.5 to 5 mols, per mol of the chromium complex.

The catalyst of the invention for trimerization of ethylene comprising (a) a chromium complex of formula (1) having a neutral multidentate ligand having a tripod structure, (b) an alkyl metal compound, (c) an optional compound selected from aromatic tertiary amine compounds, except for an imine, and nitrogen-containing heterocyclic compounds, and (d) an optional radical anion compound is prepared by contacting (a) and (b) ingredients, and optional ingredients (c) and (d), with each other in a solvent. The procedure for contacting these ingredients with each other is not particularly limited.

The concentration of the chromium complex (a) in the solvent is not particularly limited, but is usually in the range of 0.001 micro-mol to 100 milli-mol, preferably 0.01 micro-mol to 10 milli-mol. When the concentration of the chromium complex (a) is too small, a catalyst having a sufficiently high activity cannot be obtained. In contrast, when the concentration exceeds 100 milli-mol, the catalyst activity is not enhanced and the catalyst becomes costly.

As examples of the solvent used, there can be mentioned aliphatic hydrocarbons such as butane, pentane, hexane, heptane, octane, isooctane, nonane, decane, cyclopentane, cyclohexane, methylcyclohexane, cyclooctane and decaline; aromatic hydrocarbons such as benzene, toluene, xylene, ethylbenzene, cumene and trimethylbenzene; and halogenated hydrocarbons such as methylene chloride, chloroform, carbon tetrachloride, dichlorethane, chlorobenzene and dichlorobenzene. The reaction product obtained by trimerization of ethylene, namely, 1-hexene, can also be used as a solvent. These solvents may be used either alone or in combination.

To control the concentration of the chromium complex (a) in the catalyst for trimerization of ethylene, the solution of (a) in solvent may be concentrated or diluted.

The contact of (a) and (b), and optional (c) and (d) is carried out usually at a temperature of −100 to 250° C., preferably 0 to 200° C. The contact time is not particularly limited, but is usually in the range of 1 minute to 24 hours, preferably 2 minutes to 2 hours. The operation for the contact of (a), (b), (c) and (d) is preferably carried out under conditions such that these ingredients are not in contact with air and moisture. The ingredients (a), (b), (c) and (d) used are preferably preliminarily dried.

Trimerization of Ethylene

The trimerization of ethylene is carried out by contacting ethylene with the above-mentioned catalyst comprising ingredients (a) and (b), and optional ingredients (c) and (d). The procedure for contacting ethylene with the catalyst is not particularly limited, and there can be mentioned a first procedure wherein ingredients (a) and (b) and optional ingredients (c) and (d) are contacted together in the presence of ethylene whereby the catalyst is prepared and simultaneously the trimerization of ethylene is commenced; and a second procedure wherein ingredients (a) and (b) and optional ingredients (c) and (d) are preliminarily contacted together to prepare the catalyst, and then, ethylene is placed in contact with the catalyst to effect trimerization.

More specifically, the first procedure includes (i) a procedure wherein ingredients (a) and (b), optional ingredients (c) and (d), and ethylene are simultaneously and separately introduced in a reaction system; (ii) a procedure wherein ingredient (a), optional ingredients (c) and (d), and ethylene are introduced in a solution of ingredient (b); (iii) ingredient (b) and ethylene are introduced in a solution containing ingredient (a) and optional ingredients (c) and (d); (iv) ingredient (a) and ethylene are introduced in a solution containing ingredient (b) and optional ingredients (c) and (d): (v) a procedure wherein ingredient (b), optional ingredients (c) and (d), and ethylene are introduced in a solution of ingredient (a). The second procedure includes (i) a procedure wherein ingredient (b) is introduced in a solution containing ingredient (a) and optional Ingredients (c) and (d), then, ethylene is introduced in the solution; (ii) a procedure wherein ingredient (a) is introduced in a solution containing ingredient (b) and optional ingredients (c) and (d), then, ethylene is introduced in the solution; (iii) a procedure wherein ingredient (a) and optional ingredients (c) and (d) are introduced in a solution of ingredient (b), then, ethylene is introduced in the solution; and ethylene is introduced into the solution; and (iv) a procedure wherein ingredient (b) and optional ingredients (c) and (d) are introduced in a solution of ingredient (a), then, ethylene is introduced in the solution.

To enhance the catalyst activity, the trimerization of ethylene can be conducted while the catalyst comprising ingredients (a) and (b) and optional ingredients (c) and (d) is irradiated with light.

The light employed is not particularly limited, and includes, for example, ultraviolet light, visible light and infrared light. The emission wavelength is preferably in the range of 0.2 to 2,000 nm and more preferably 200 to 700 nm. The illuminace is not particularly limited.

Sun light and an artificial light source can be employed, but, the latter light source is preferable because the illuminance of the former is poor, and varies depending upon the weather and time. As specific examples of the artificial light source, there can be mentioned a heavy hydrogen lamp, a xenon lamp, a tungsten lamp, an incandescent lamp, a halogen lamp, a low pressure mercury lamp, a hollow cathode lamp, a metal vapor discharge tube, a metal halide lamp, high-pressure sodium lamp, a thallium lamp, a mercury-thallium lamp, a mercury-lead lamp, an H-type discharge tube, a xenon-mercury lamp, a high pressure mercury lamp, an ultra-high pressure mercury lamp and a flash lamp.

The irradiation with light can be conducted by irradiating the catalyst or the reaction mixture for trimerization of ethylene. More specifcally, the procedure for Irradiating the catalyst with light includes (i) a procedure wherein a solution of ingredient (a) is irradiated with light, and then, ingredient (b), and optional ingredient (c) and (d) are introduced in the solution, followed by introduction of ethylene; and (ii) a procedure wherein a solution containing ingredients (a) and (b) and optional ingredient (c) and (d) is irradiated with light, and then, ethylene is introduced in the solution and trimerized therein. The procedure for irradiating the reaction mixture for trimerization includes (i) a procedure wherein ethylene is trimerized while being irradiated with light in the presence of ingredients (a) and (b) and optional ingredient (c) and (d); (ii) a procedure wherein a solution containing ingredients (a) and (b) and optional ingredient (c) and (d) is irradiated with light, and then, ethylene is introduced in the solution and trimerization of ethylene is conducted while being irradiated with light; (iii) a procedure wherein a solution of ingredient (a) is irradiated with light, and then, ingredient (b), and optional ingredient (c) and (d) are introduced in the solution, then, ethylene is trimerized while being irradiated with light; and (iv) a procedure wherein ingredients (a) and (b), optional ingredients (c) and (d), and ethylene are separately and simultaneously introduced in the reaction system where ethylene is trimerized, while the reaction system is irradiated with light; and (v) a procedure wherein ingredient (a) is preliminarily irradiated with light, and the irradiated ingredient (a), and ingredient (b) and optional ingredients (c) and (d), and ethylene are separately and simultaneously introduced in the reaction system, followed by irradiation with light. The irradiation time is not particularly limited.

The reaction temperature for trimerization of ethylene is usually in the range of −100 to 250° C., preferably 0 to 200° C. The reaction pressure is not particularly limited provided that the reaction is conducted in an ethylene atmosphere. Usually an absolute pressure of 0.01 to 3,000 kg/cm$^2$, preferably 0.1 to 300 kg/cm$^2$ is employed. The reaction time is usually in the range of 5 seconds to 6 hours, although it varies depending upon the reaction temperature and pressure.

The reaction can be conducted in a continuous manner wherein ethylene is continuously introduced so that the stated pressure is maintained, or in a batchwise manner wherein ethylene is preliminarily charged to a stated pressure, and then, the reaction is conducted, or a semi-batchwise manner. A feed of ethylene may comprise a gas inert to the reaction such as nitrogen, argon or helium. The operation for the trimerization of ethylene is preferably carried out under conditions such that ethylene and the catalyst are not in contact with air and moisture. Preferably ethylene is preliminarily thoroughly dried.

To terminate the trimerization of ethylene, a deactivator such as water, an alcohol or an aqueous sodium hydroxide solution can be added to deactivate the catalyst. The deactivated chromium complex catalyst can be removed by a known ash-removing procedure, for example, by extracting the catalyst with water or an aqueous alkali solution. The thus-produced 1-hexene is separated, for example, by a known extraction or distillation procedure. Side-reaction products such as polyethylene can be separated as a residue by a known centrifugal separation or by a known distillation of 1-hexene.

The invention will now be specifically described by the following examples that by no means limit the scope of the invention.

In the examples, determination of a chromium complex and products produced by trimerization of ethylene analysis was conducted by the following methods.

(1) Determination of Chromium Complex

A chromium complex was analyzed according to infrared (IR) absorption spectroscopy using an infrared spectrophotometer "FTIR-8100" supplied by Shimadzu Corporation. A specimen was prepared by a nujol mull method.

(2) Determination of Trimerization Products (i) Products having 4 to 8 carbon atoms contained in the reaction liquid were determined gas chromatography using a gas chromatograph "GC-14A" supplied by Shimadzu Corporation equipped with a column "TC-1" supplied by GL Science Co. The analysis was carried out using a nitrogen carrier at an injection temperature of 280° C. and a detector temperature of 280° C. n-heptane was used as internal standard. The measurement was conducted when the column temperature was elevated from 40° C. to 250° C. after 1.0 $\mu$l of a reaction liquid was introduced into the chromatograph.

(ii) Products having at least 10 carbon atoms contained in the reaction liquid were determined gas chromatography using another gas chromatograph "GC-14A" supplied by Shimadzu Corporation equipped with a column "TC-1" supplied by GL Science Co. The analysis was carried out using a nitrogen carrier at an injection temperature of 300° C. and a detector temperature of 300° C. n-heptane was used as internal standard. The measurement was conducted when the column temperature was elevated from 50° C. to 300° C. after 1.5 $\mu$l of a reaction liquid was introduced into the chromatograph.

(iii) Products contained in the gas atmosphere were determined by gas chromatography using a gas chromatograph "GC-9A" supplied by Shimadzu Corporation equipped with an Al$_2$O$_3$/KCl column supplied by Chrompack Co. The analysis was carried out using a nitrogen carrier at an injection temperature of 200° C., a detector temperature of 200° C. and a column temperature of 120° C. Absolute calibration curve was used. The measurement was conducted by introducing 0.2 ml of the collected gas into the chromatograph.

REFERENCE EXAMPLE 1

A Schlenk tube having an inner volume of 100 ml was charged with 238 mg of tris(3,5-dimethyl-1-pyrazolyl) methane having a tripod structure, which was synthesized by a method described in J. Amer. Chem. Soc., 92, 5118 (1970), 176 mg of chromium hexacarbonyl, 40 ml of mesitylene and 10 ml of toluene. The content was heated under reflux in a nitrogen atmosphere for 1 hour while being stirred. The thus-precipitated crystal was recovered by filtration to give tris(3,5-dimethyl-1-pyrazolyl)methanechromium tricarbonyl(0) (hereinafter referred to as "complex A"). IR analysis of complex A revealed that two peaks were found at 1896 cm$^{-1}$ and 1759 cm$^{-1}$ due to the absorption of CO and thus that tris(3,5-dimethyl-1-pyrazolyl)methane is facially coordinated to chromium. When complex A was exposed to the air, any qualitative change was not observed.

REFERENCE EXAMPLE 2

A Schlenk tube having an inner volume of 100 ml was charged with 312 mg of 1,1,1-tris(diphenylphosphinomethyl)ethane having a tripod structure (supplied by Aldrich Co.), 110 mg of chromium hexacarbonyl and 50 ml of decalin. The content was heated under reflux in a nitrogen atmosphere for 1 hour while being stirred. The thus-precipitated crystal was recovered by filtration to give 1,1,1-tris(diphenylphosphinomethyl) ethanechromium tricarbonyl(0) (hereinafter referred to as "complex B"). IR analysis of complex B revealed that two peaks were found at 1933 cm$^{-1}$ and 1840 cm$^{-1}$ due to the absorption of CO and thus that 1,1,1-tris(diphenylphosphinomethyl)ethane is facially coordinated to chromium. When complex B was exposed to the air, any qualitative change was not observed.

REFERENCE EXAMPLE 3

A Schlenk tube having an inner volume of 100 ml was charged with 95 mg of diphenylmethylphosphine, 443 mg of (cycloheptatriene)chromium tricarbonyl and 15 ml of toluene. The content was heated under reflux in a nitrogen atmosphere for 2 hours while being stirred. Toluene was distilled off to give tris(diphenylmethylphosphine) chromium tricarbonyl(0) (hereinafter referred to as "complex D"). IR analysis of complex D revealed that four peaks were found at 1948 cm$^{-1}$, 1891 cm$^{-1}$, 1856 cm$^{-1}$ and 1838 cm$^{-1}$ due to the absorption of CO and thus that three ligands of diphenylmethylphosphine were meridionally coordinated to chromium.

REFERENCE EXAMPLE 4

A Schlenk tube having an inner volume of 100 ml was charged with 199 mg of bis(diphenylphosphino)ethane, 110 mg of chromium hexacarbonyl and 50 ml of decalin. The content was heated under reflux in a nitrogen atmosphere for 1.5 hours while being stirred. The thus-precipitated crystal was recovered by filtration to give bis(diphenylphosphino) ethanechromium tricarbonyl(0) (hereinafter referred to as "complex E"). IR analysis of complex E revealed that four peaks were found at 2012 cm$^{-1}$, 1925 cm$^{-1}$, 1910 cm$^{-1}$ and 1896 cm$^{-1}$ due to the absorption of CO and thus that bis(diphenylphosphino)ethane was coordinated to chromium.

REFERENCE EXAMPLE 5

A Schlenk tube having an inner volume of 100 ml was charged with 126 mg of tris(3,5-dimethyl-1-pyrazolyl) methane having a tripod structure, which was synthesized by a method described in J. Amer. Chem. Soc., 92, 5118 (1970), 143 mg of tris(tetrahydrofuran)chromium trichloride(III), and 20 ml of tetrahydrofuran. The content was heated in a nitrogen atmosphere for 12 hours while being stirred. The thus-precipitated crystal was recovered by filtration to give tris(3,5-dimethyl-1-pyrazolyl)methanechromium trichloride (III) (hereinafter referred to as "complex F").

A Schlenk tube was charged with 90 mg of complex F, 0.36 ml of a solution of 2.0M of lithiumdiisopropylamide/ ethylbenzene-tetrahydrofuran and 10 ml of toluene. The content was heated in a nitrogen atmosphere for 12 hours while being stirred. The reaction liquid was filtered and the solvent was removed by drying under a reduced pressure to give tris(3,5-dimethyl-1-pyrazolyl)methane-tris (diisopropylamide)chromium (III) (hereinafter referred to as "complex G").

REFERENCE EXAMPLE 6

A Schlenk tube having an inner volume of 200 ml provided with a magnetic rotor was charged with 12.8 g of naphthalene and 100 ml of ethylene glycol dimethyl ether in a nitrogen atmosphere. Then 2.5g of sodiummetal was added, and the content was stirred at room temperature for 3 hours. The thus-produced sodium naphthalene was titrated with a solution of 0.5 mol/l of 1-menthol in ethylene glycol dimethyl ether. The concentration of sodium naphthalene was proved to be 1.0 mol/l.

EXAMPLE 1

A pressure-resistant glass reactor having an inner volume of 150 ml, provided with a thermometer and a stirring apparatus was charged with 6.9 mg of complex A, prepared in Reference Example 1, 1.6 ml of a solution of triisobutylaluminum/cyclohexane having a concentration of 0.154 mol/l, and 80 ml of dry toluene, and the content was stirred.

The reactor was heated to 80° C. and the rate of stirring was adjusted to 1,400 rpm, and ethylene was introduced in the reactor. The content was irradiated with light by using an ultra-high pressure mercury lamp (500 W) supplied by Ushio Inc. to effect trimerization of ethylene. Ethylene was introduced to an extent such that the absolute pressure within the reactor reached 5 kg/cm$^3$ and the introduction of ethylene was continued so that this pressure was maintained during the reaction. When 30 minutes elapsed while the temperature was maintained at 80° C., water was injected by nitrogen into the reactor to deactivate the catalyst and terminate the reaction.

The reactor was cooled to room temperature and then the pressure was reduced to normal pressure. The products contained in the reaction liquid and in the gas collected from the reactor were analyzed by gas chromatography. The solid contained in the reaction liquid was filtered by filter paper. The collected solid was air-dried and further dried under a reduced pressure of 1 mmHg at 100° C., and then weighed. The results are shown in Table 1.

EXAMPLE 2

Trimerization of ethylene was conducted by the same procedure as in Example 1 except that cyclohexane was used instead of toluene with all other conditions remaining the same. The results are shown in Table 1.

EXAMPLE 3

A pressure-resistant glass reactor having an inner volume of 150 ml, provided with a thermometer and a stirring apparatus was charged with 3.5 mg of complex A, prepared in Reference Example 1, 1.6 ml of a solution of triisobutylaluminum/cyclohexane having a concentration of 0.154 mol/l, and 40 ml of dry toluene, and the content was stirred.

The reactor was heated to 80° C. and the rate of stirring was adjusted to 1,400 rpm, and ethylene was introduced in the reactor to an extent such that the absolute pressure within the reactor reached 5 kg/cm². The content was irradiated with light for 5 minutes by using an ultra-high pressure mercury lamp (500 W) supplied by Ushio Inc. to commence trimerization of ethylene. Then 40 ml of dry toluene was injected into the reactor by ethylene. Ethylene was continuously introduced so that the absolute pressure within the reactor was maintained at 5 kg/cm² during the reaction. When 30 minutes elapsed while the temperature was maintained at 80° C., water was injected by nitrogen into the reactor to deactivate the catalyst and terminate the reaction.

The reactor was cooled to room temperature and then the pressure was reduced to normal pressure. The products contained in the reaction liquid and in the gas collected from the reactor were analyzed by gas chromatography. The solid contained in the reaction liquid was filtered by filter paper. The collected solid was air-dried and further dried under a reduced pressure of 1 mmHg at 100° C., and then weighed. The results are shown in Table 1.

EXAMPLES 4–6

Trimerization of ethylene was conducted by the same procedure as in Example 3 except that the amounts of complex A and triisobutylaluminum charged were varied as shown in Table 1 with all other conditions remaining the same. The results are shown in Table 1.

TABLE 1

| Example | | 1 | 2 | 3 | 4 | 5 | 6 |
|---|---|---|---|---|---|---|---|
| Catalyst: | | | | | | | |
| Cr complex | | A | A | A | A | A | A |
|  | (μmol) | 16.0 | 16.0 | 8.0 | 4.0 | 1.0 | 4.0 |
| Alkyl metal compound | | i-Bu₃Al | i-Bu₃Al | i-Bu₃Al | i-Bu₃Al | i-Bu₃Al | i-Bu₃Al |
|  | (μmol) | 240 | 240 | 240 | 240 | 240 | 480 |
| Solvent | | Toluene | CyHe | Toluene | Toluene | Toluene | Toluene |
| Reaction conditions: | | | | | | | |
| Temperature | (° C.) | 80 | 80 | 80 | 80 | 80 | 80 |
| Pressure | (kg/cm²) | 5 | 5 | 5 | 5 | 5 | 5 |
| Time | (min) | 30 | 30 | 30 | 30 | 30 | 30 |
| Results: | | | | | | | |
| Catalytic activity | (g-1-hexene/g-Cr. h) | 445 | 281 | 1,830 | 3,870 | 6,780 | 4,870 |
| Liquid | (wt. %) | 99.0 | 96.9 | 99.8 | 99.1 | 98.9 | >99.9 |
| Solid (PE) | (wt. %) | 1.0 | 3.1 | 0.2 | 0.9 | 1.1 | trace |
| Products in liquid: | | | | | | | |
| C4 | (wt. %) | 4.4 | 5.8 | 2.6 | 0.2 | 1.7 | 2.4 |
| C6 | (wt. %) | 77.9 | 76.3 | 91.8 | 96.1 | 97.1 | 95.6 |
| C8 | (wt. %) | 2.3 | 5.1 | 0.8 | 0.5 | 0.3 | 0.2 |
| C10 | (wt. %) | 5.6 | 5.3 | 2.4 | 1.9 | 0.8 | 1.4 |
| C12+ | (wt. %) | 9.8 | 7.5 | 2.4 | 1.3 | 0.1 | 0.4 |
| Purity of C6 | (wt. %) | 96.2 | 95.4 | 98.9 | 99.1 | 99.3 | 99.1 |

Note
C4: Butene,
C6: Hexene,
C8: Octene,
C10: Decene,
C12+: Dodecene and higher olefins,
PE: Polyethylene,
Purity of C6: (1-hexene/sum of hexene isomers) × 100,
CyHe: Cyclohexane,
i-Bu₃Al: Triisobutylaluminum

EXAMPLES 7

Trimerization of ethylene was conducted by the same procedure as in Example 3 except that triethylaluminum was used instead of triisobutylaluminum with all other conditions remaining the same. The results are shown in Table 2.

EXAMPLES 8

Trimerization of ethylene was conducted by the same procedure as in Example 3 except that tris(n-hexyl) aluminum was used instead of triisobutylaluminum with all other conditions remaining the same. The results are shown in Table 2.

EXAMPLES 9

Trimerization of ethylene was conducted by the same procedure as in Example 1 except that 12.2 mg of complex B, prepared in Reference Example 2, was used instead of complex A, and cyclohexane was used instead of toluene with all other conditions remaining the same. The results are shown in Table 2.

COMPARATIVE EXAMPLES 1

Trimerization of ethylene was conducted by the same procedure as described in Example 1 except that 4.1 mg of commercially available mesitylenechromium tricarbonyl(0) (hereinafter referred to as "complex C") was used instead of complex A with all other conditions remaining the same. The results are shown in Table 2.

COMPARATIVE EXAMPLES 2

Trimerization of ethylene was conducted by the same procedure as in Example 1 except that 11.8 mg of complex D, prepared in Reference Example 3, was used instead of complex A, and cyclohexane was used instead of toluene with all other conditions remaining the same. The results are shown in Table 2.

COMPARATIVE EXAMPLES 3

Trimerization of ethylene was conducted by the same procedure as in Example 1 except that 9.0 mg of complex E, prepared in Reference Example 4, was used instead of complex A, and cyclohexane was used instead of toluene with all other conditions remaining the same. The results are shown in Table 2.

EXAMPLE 10

A pressure-resistant glass reactor having an inner volume of 150 ml, provided with a thermometer and a stirring apparatus was charged with 10.4 mg of complex G, prepared in Reference Example 5, and 80 ml of dry toluene, and the content was stirred.

The reactor was heated to 80° C. and the rate of stirring was adjusted to 1,400 rpm, and 1.6 ml of a solution of triisobutylaluminum/cyclohexane having a concentration of 0.154 mol/l was introduced by the pressure of ethylene, whereby trimerization of ethylene was commenced. The amount of ethylene introduced was controlled so that the absolute pressure within the reactor reached 5 kg/cm$^2$ and the introduction of ethylene was continued so that this pressure was maintained during the reaction. When 30 minutes elapsed while the temperature was maintained at 80° C., water was injected by nitrogen into the reactor to deactivate the catalyst and terminate the reaction.

The reactor was cooled to room temperature and then the pressure was reduced to normal pressure. The products contained in the reaction liquid and in the gas collected from the reactor were analyzed by gas chromatography. The results are shown in Table 3.

TABLE 2

| | | Example | | | Comparative Example | | |
|---|---|---|---|---|---|---|---|
| | | 7 | 8 | 9 | 1 | 2 | 3 |
| Catalyst: | | | | | | | |
| Cr complex | | A | A | B | C | D | E |
| | ($\mu$mol) | 4.0 | 4.0 | 16.0 | 16.0 | 16.0 | 16.0 |
| Alkyl metal compound | | Et$_3$Al | Hex$_3$Al | i-Bu$_3$Al | i-Bu$_3$Al | i-Bu$_3$Al | i-Bu$_3$Al |
| | ($\mu$mol) | 480 | 480 | 240 | 240 | 240 | 240 |
| Solvent | | Toluene | Toluene | CyHe | Toluene | CyHe | CyHe |
| Reaction conditions: | | | | | | | |
| Temperature | (° C.) | 80 | 80 | 80 | 80 | 80 | 80 |
| Pressure | (kg/cm$^2$) | 5 | 5 | 5 | 5 | 5 | 5 |
| Time | (min) | 30 | 30 | 30 | 30 | 30 | 30 |
| Results: | | | | | | | |
| Catalytic activity | (g-1-hexene/g-Cr. h) | 3,280 | 3,380 | 76 | 176 | 230 | 201 |
| Liquid | (wt. %) | >99.0 | 99.9 | 91.1 | 87.1 | 60.6 | 38.2 |
| Solid (PE) | (wt. %) | trace | 0.1 | 8.9 | 12.9 | 39.4 | 61.8 |
| Products in liquid: | | | | | | | |
| C4 | (wt. %) | 7.3 | 0.8 | 12.2 | 4.9 | 12.4 | 0.9 |
| C6 | (wt. %) | 90.5 | 87.8 | 51.0 | 68.4 | 63.1 | 90.3 |
| C8 | (wt. %) | 0.5 | 1.7 | 13.3 | 5.5 | 4.4 | 6.0 |
| C10 | (wt. %) | 1.6 | 5.3 | 11.1 | 7.7 | 5.2 | 1.1 |
| C12+ | (wt. %) | 0.2 | 4.5 | 12.4 | 13.4 | 14.9 | 1.7 |
| Purity of C6 | (wt. %) | 98.8 | 97.5 | 90.3 | 98.5 | 97.6 | >99.9 |

Note
C4: Butene,
C6: Hexene,
C8: Octene,
C10: Decene,
C12+: Dodecene and higher olefins,
PE: Polyethylene,
Purity of C6: (1-hexene/sum of hexene isomers) × 100,
CyHe: Cyclohexane
i-Bu$_3$Al: Triisobutylaluminum,
Et$_3$Al: Triethylaluminum,
Hex$_3$Al: Tris(n-hexyl)aluminum

TABLE 3

| Example | 10 |
|---|---|
| Catalyst: | |
| Cr complex | G |
| (μmol) | 16.0 |
| Alkyl metal compound | i-Bu$_3$Al |
| (μmol) | 240 |
| Solvent | Toluene |
| Reaction conditions: | |
| Temperature (° C.) | 80 |
| Pressure (kg/cm$^2$) | 5 |
| Time (min) | 30 |
| Results: | |
| Catalytic activity | 80 |
| (g-1-hexene/g-Cr · h) | |
| Products in liquid: | |
| C4 (wt. %) | 27.0 |
| C6 (wt. %) | 67.1 |
| C8 (wt. %) | 4.4 |
| C10 (wt. %) | 1.6 |
| C12+ (wt. %) | 0.0 |

Note Abbreviations are the same as defined in the preceding tables

EXAMPLE 11

A stainless steel reactor having an inner volume of 50 ml was charged with 1.4 ml of a solution of N,N-diemthylaniline/toluene solution having a concentration of 0.028 mol/l, and 40 ml of dry toluene (the resultant solution is hereinafter referred to as "solution A").

A pressure-resistant glass reactor having an inner volume of 150 ml, provided with a thermometer and a stirring apparatus was charged with 1.7 mg of complex A, prepared in Reference Example 1, 2.0 ml of a solution of triisobutylaluminum/cyclohexane having a concentration of 0.24 mol/l, and 40 ml of dry toluene, and the content was stirred.

The reactor was heated to 80° C. and the rate of stirring was adjusted to 1,400 rpm, and ethylene was introduced in the reactor to an extent such that the absolute pressure within the reactor reached 5 kg/cm$^2$. The content was irradiated with light for 5 minutes by using an ultra-high pressure mercury lamp (500 W) supplied by Ushio Inc., and then, solution A was injected by ethylene into the reactor. Ethylene was continuously introduced so that the inner absolute pressure was maintained at 5 kg/cm$^2$, while the temperature was maintained at 80° C. When 30 minutes elapsed, water was injected by nitrogen into the reactor to deactivate the catalyst and terminate the reaction.

The reactor was cooled to room temperature and then the pressure was reduced to normal pressure. The products contained in the reaction liquid and in the gas collected from the reactor were analyzed by gas chromatography. The solid contained in the reaction liquid was filtered by filter paper. The collected solid was air-dried and further dried under a reduced pressure of 1 Torr at 100° C., and then weighed. The results are shown in Table 4.

EXAMPLE 12

Trimerization of ethylene was conducted by the same procedure as in Example 11 except that 0.29 ml of a solution of N,N-dimethylaniline/toluene having a concentration of 0.028 mol/l was used instead of 1.4 ml of the same solution with all other conditions remaining the same. The results are shown in Table 4.

EXAMPLE 13

Trimerization of ethylene was conducted by the same procedure as in Example 11 except that 2.9 ml of a solution of N,N-dimethylaniline/toluene having a concentration of 0.028 mol/l was used instead of 1.4 ml of the same solution with all other conditions remaining the same. The results are shown in Table 4.

EXAMPLE 14–16

Trimerization of ethylene was repeated by the same procedure as in Example 11 except that each of the aromatic tertiary amines shown in Table 4 was used instead of N,N-dimethylaniline with all other conditions remaining the same. The results are shown in Table 4.

TABLE 4

| Example | | 11 | 12 | 13 | 14 | 15 | 16 |
|---|---|---|---|---|---|---|---|
| Catalyst: | | | | | | | |
| Cr complex | | A | A | A | A | A | A |
| | (μmol) | 4.0 | 4.0 | 4.0 | 4.0 | 4.0 | 4.0 |
| Alkyl metal compound | | i-Bu$_3$Al | i-Bu$_3$Al | i-Bu$_3$Al | i-Bu$_3$Al | i-Bu$_3$Al | i-Bu$_3$Al |
| | (μmol) | 480 | 480 | 480 | 480 | 480 | 480 |
| Tertery aromatic amine | | PhNMe$_2$ | PhNMe$_2$ | PhNMe$_2$ | PhN(Pr-n)$_2$ | Ph$_2$NMe | Ph$_3$N |
| | (μmol) | 40 | 8 | 80 | 40 | 40 | 40 |
| Solvent | | Toluene | Toluene | Toluene | Toluene | Toluene | Toluene |
| Reaction conditions: | | | | | | | |
| Temperature | (° C.) | 80 | 80 | 80 | 80 | 80 | 80 |
| Pressure | (kg/cm$^2$) | 5 | 5 | 5 | 5 | 5 | 5 |
| Time | (min) | 30 | 30 | 30 | 30 | 30 | 30 |
| Results: | | | | | | | |
| Catalytic activity | (g-1-hexene/g-Cr. h) | 12,600 | 8,380 | 13,000 | 11,900 | 9,050 | 15,600 |
| Liquid | (wt. %) | 99.9 | >99.9 | 99.9 | 99.7 | >99.9 | >99.9 |
| Solid (PE) | (wt. %) | 0.1 | trace | 0.1 | 0.3 | trace | trace |
| Products in liquid: | | | | | | | |
| C4 | (wt. %) | 1.2 | 1.6 | 1.1 | 0.9 | 1.5 | 1.0 |
| C6 | (wt. %) | 97.6 | 96.5 | 96.9 | 96.6 | 96.4 | 97.0 |
| C8 | (wt. %) | 0.2 | 0.1 | 0.2 | 0.2 | 0.1 | 0.2 |

TABLE 4-continued

| Example | | 11 | 12 | 13 | 14 | 15 | 16 |
|---|---|---|---|---|---|---|---|
| C10 | (wt. %) | 0.6 | 1.3 | 1.1 | 1.2 | 1.1 | 1.1 |
| C12+ | (wt. %) | 0.4 | 0.5 | 0.7 | 1.2 | 0.8 | 0.7 |
| Purity of C6 | (wt. %) | 99.1 | 99.1 | 99.1 | 99.2 | 99.2 | 99.1 |

Note
PhNMe$_2$: N,N-dimethylaniline,
PhN(Pr-n)$_2$: N,N-bis(n-propyl)aniline,
Ph$_2$NMe: Methyldiphenylamine,
Ph$_3$N: Triphenylamine,
Other abbreviations are the same as defined in the preceding tables.

COMPARATIVE EXAMPLE 4

Trimerization of ethylene was conducted by the same procedure as in Example 11 except that N,N-dimethylaniline was not used with all other conditions remaining the same. The results are shown in Table 5.

COMPARATIVE EXAMPLE 5

Trimerization of ethylene was conducted by the same procedure as in Example 11 except that 12 mg of N,N-dimethyloctadecylamine, i.e., a tertiary aliphatic amine, was used instead of N,N-dimethylaniline with all other conditions remaining the same. The results are shown in Table 5.

COMPARATIVE EXAMPLE 6

Trimerization of ethylene was conducted by the same procedure as in Example 11 except that 14 mg of didodecylamine, i.e., a secondary aliphatic amine, was used instead of N,N-dimethylaniline with all other conditions remaining the same. The results are shown in Table 5.

TABLE 5

| Comparative Example | 4 | 5 | 6 |
|---|---|---|---|
| Catalyst: | | | |
| Cr complex | A | A | A |
| ($\mu$mol) | 4.0 | 4.0 | 4.0 |
| Alkyl metal compound | i-Bu$_3$Al | i-Bu$_3$Al | i-Bu$_3$Al |
| ($\mu$mol) | 480 | 480 | 480 |
| Tertiary aromatic amine | — | C$_{18}$H$_{37}$NME$_2$ | (C$_{12}$H$_{25}$)$_2$NH |
| ($\mu$mol) | — | 40 | 40 |
| Solvent | Toluene | Toluene | Toluene |
| Reaction conditions: | | | |
| Temperature (° C.) | 80 | 80 | 80 |
| Pressure (kg/cm$^2$) | 5 | 5 | 5 |
| Time (min) | 30 | 30 | 30 |
| Results: | | | |
| Catalytic activity (g-1-hexene/g-Cr · h) | 4,870 | 5,000 | 4,330 |
| Liquid (wt. %) | >99.9 | 99.0 | >99.9 |
| Solid (wt. %) | trace | 1.0 | trace |
| Products in liquid: | | | |
| C4 (wt. %) | 2.4 | 1.9 | 2.7 |
| C6 (wt. %) | 95.6 | 94.4 | 95.0 |
| C8 (wt. %) | 0.2 | 0.2 | 0.2 |
| C10 (wt. %) | 1.4 | 1.8 | 1.3 |
| C12+ (wt. %) | 0.4 | 1.7 | 0.8 |
| Purity of C6 (wt. %) | 99.1 | 99.1 | 99.1 |

Note C$_{18}$H$_{37}$NME$_2$: N,N-Dimethyloctadecylamine, (C$_{12}$H$_{25}$)$_2$NH: N,N-Didocylamine
Other abbreviations are the same as defined in the preceding tables

EXAMPLE 17

A pressure-resistant glass reactor having an inner volume of 150 ml, provided with a thermometer and a stirring apparatus was charged with 7.3 mg of complex F, prepared in Reference Example 5, and 80 ml of dry toluene, and the content was stirred.

The reactor was heated to 80° C. and the rate of stirring was adjusted to 1,400 rpm, and 1.6 ml of a solution of triisobutylaluminum/cyclohexane having a concentration of 0.150 mol/l was introduced by the pressure of ethylene, whereby trimerization of ethylene was commenced. Ethylene was introduced to an extent such that the absolute pressure within the reactor reached 5 kg/cm$^2$, and the introduction of ethylene was continued so that this pressure was maintained during the reaction. When 30 minutes elapsed while the temperature was maintained at 80° C., water was injected by nitrogen into the reactor to deactivate the catalyst and terminate the reaction.

The reactor was cooled to room temperature and then the pressure was reduced to normal pressure. Any solids such as polyethylene were not found in the reaction liquid. The products contained in the reaction liquid and in the gas collected from the reactor were analyzed by gas chromatography. The results are shown in Table 6.

EXAMPLE 18

Trimerization of ethylene was conducted by the same procedure as described in Example 17 except that 1.5 ml of a solution of n-butyllithium/cyclohexane having a concentration of 53.3 mmol/l was added prior to the addition of the solution of triisobutylaluminum/cyclohexane with all other conditions remaining the same. The results are shown in Table 6.

TABLE 6

| Example | 17 | 18 |
|---|---|---|
| Catalyst: | | |
| Cr complex | F | F |
| ($\mu$mol) | 16.0 | 16.0 |
| Alkyl metal compound | i-Bu$_3$Al | i-Bu$_3$Al |
| ($\mu$mol) | 240 | 240 |
| | | n-BuLi |
| | | 80 |
| Solvent | Toluene | Toluene |
| Reaction conditions: | | |
| Temperature (° C.) | 80 | 80 |
| Pressure (kg/cm$^2$) | 5 | 5 |
| Time (min) | 30 | 30 |

TABLE 6-continued

| Example | 17 | 18 |
|---|---|---|
| Results: | | |
| Catalytic activity (g-1-hexene/g-Cr · h) | 3.0 | 18 |
| Products in liquid: | | |
| C4 (wt. %) | 49.5 | 71.5 |
| C6 (wt. %) | 36.3 | 23.4 |
| C8 (wt. %) | 0.0 | 4.0 |
| C10 (wt. %) | 14.3 | 1.2 |
| C12+ (wt. %) | 0.0 | 0.0 |
| Purity of C6 (wt. %) | >99.9 | 92.9 |

Note n-BuLi: n-butyllithium, Other abbreviations are the same as defined in the preceding tables

EXAMPLE 19

A pressure-resistant glass reactor having an inner volume of 150 ml, provided with a thermometer and a stirring apparatus was charged with 3.6 mg of complex F, prepared in Reference Example 5, 80 ml of dry toluene and 0.012 ml of a solution of sodium naphthalene/ethylene glycol dimethyl ether having a concentration of 1 mol/l, and the content was stirred.

The reactor was heated to 80° C. and the rate of stirring was adjusted to 1,100 rpm, and 4.0 ml of a solution of triisobutylaluminum/toluene having a concentration of 0.240 mol/l was introduced by the pressure of ethylene, whereby trimerization of ethylene was commenced. Ethylene was introduced to an extent such that the absolute pressure within the reactor reached 5 kg/cm$^2$, and the introduction of ethylene was continued so that this pressure was maintained during the reaction. When 30 minutes elapsed while the temperature was maintained at 80° C., water was injected by nitrogen into the reactor to deactivate the catalyst and terminate the reaction.

The reactor was cooled to room temperature and then the pressure was reduced to normal pressure. Any solids such as polyethylene were not found in the reaction liquid. The products contained in the reaction liquid and in the gas collected from the reactor were analyzed by gas chromatography. The results are shown in Table 7.

EXAMPLE 20

Trimerization of ethylene was conducted by the same procedure as described in Example 19 except that the amount of the triisobutylaluminum/toluene solution was changed to 2.4 ml with all other conditions remaining the same. The results are shown in Table 7.

TABLE 7

| Example | 19 | 20 |
|---|---|---|
| Catalyst: | | |
| Cr complex | F | F |
| ($\mu$mol) | 4.0 | 4.0 |
| Alkyl metal compound | i-Bu$_3$Al | i-Bu$_3$Al |
| ($\mu$mol) | 960 | 590 |
| Radical anion | Na-na | Na-na |
| ($\mu$mol) | 12 | 12 |
| Solvent | Toluene | Toluene |
| Reaction conditions: | | |
| Temperature (° C.) | 80 | 80 |
| Pressure (kg/cm$^2$) | 5 | 5 |
| Time (min) | 30 | 30 |
| Results: | | |
| Catalytic activity (g-1-hexene/g-Cr · h) | 5,490 | 4,750 |
| Products in liquid: | | |
| C4 (wt. %) | 2.4 | 1.8 |
| C6 (wt. %) | 96.1 | 97.0 |
| C8 (wt. %) | 0.2 | 0.0 |
| C10 (wt. %) | 0.9 | 0.8 |
| C12+ (wt. %) | 0.4 | 0.4 |
| Purity of C6 (wt. %) | 99.1 | 99.2 |

Note Na-na: Sodium naphthalene, Other abbreviations are the same as defined in the preceding tables

EXAMPLE 21

A Schlenk tube having an inner volume of 20 ml was charged with 12.1 mg of complex G, prepared in Reference Example 5, and 15.7 ml of a solution of triisobutylaluminum/toluene having a concentration of 0.238 mol/l, and the content was stirred.

A pressure-resistant glass reactor having an inner volume of 150 ml, provided with a thermometer and a stirring apparatus was charged with 4.0 ml of the above-mentioned solution and 80 ml of dry toluene, and the content was stirred. Ethylene was introduced in the reactor to an extent such that the absolute pressure within the reactor reached 5 kg/cm$^2$, and the pressure was maintained at 5 kg/cm$^2$ during the reaction. When 30 minutes elapsed, water was injected by nitrogen into the reactor to deactivate the catalyst and terminate the reaction.

The reactor was cooled to room temperature and then the pressure was reduced to normal pressure. The products contained in the reaction liquid and in the gas collected from the reactor were analyzed by gas chromatography. The results are shown in Table 8.

TABLE 8

| Example | 21 |
|---|---|
| Catalyst: | |
| Cr complex | G |
| ($\mu$mol) | 4.0 |
| Alkyl metal compound | i-Bu$_3$Al |
| ($\mu$mol) | 960 |
| Solvent | Toluene |
| Reaction conditions: | |
| Temperature (° C.) | 80 |
| Pressure (kg/cm$^2$) | 5 |
| Time (min) | 30 |
| Results: | |
| Catalytic activity (g-1-hexene/g-Cr · h) | 1,637 |

TABLE 8-continued

| Example | 21 |
|---|---|
| Oligomers (wt. %) | 98.3 |
| Solid (PE) (wt. %) | 1.7 |
| Products in oligomers: | |
| C4 (wt. %) | 3.0 |
| C6 (wt. %) | 94.9 |
| C8 (wt. %) | 0.0 |
| C10 (wt. %) | 0.4 |
| C12+ (wt. %) | 0.0 |
| Purity of C6 (wt. %) | 99.4 |

Note Abbreviations are the same as defined in the preceding tables

What is claimed is:

1. A catalyst for trimerization of ethylene which comprises:

(a) a chromium complex having a neutral multidentate ligand having a tripod structure, represented by the following formula (1):

$$ACrJ_nQ_{3-n} \tag{1}$$

wherein A is a neutral multidentate ligand having a tripod structure, J is a carbonyl ligand or a halogen atom, n is an integer of 0 to 3, and Q is at least one member selected from the group consisting of a hydrogen atom, a hydrocarbon group having 1 to 10 carbon atoms, a carboxylate group having 1 to 10 carbon atoms, a diketonato group having 3 to 10 carbon atoms, an amide group, an imide group, an alkoxide group having 1 to 10 carbon atoms, a thioalkoxide group having 1 to 10 carbon atoms, an arene ligand having 6 to 15 carbon atoms, an alkene ligand having 2 to 10 carbon atoms, an alkene ligand having 2 to 15 carbon atoms, an amine ligand, an imine ligand, a nitrile ligand, an isonitrile ligand, a phosphine ligand, a phosphine oxide ligand, a phosphite ligand, an ether ligand, a sulfide ligand, a sulfone ligand and a sulfoxide ligand, and (b) an alkyl group containing compound;
said neutral multidentate ligand A in formula (1) being represented by the following formula (2) or formula (3):

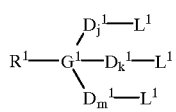
(2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms or an aryl group having 6 to 10 carbon atoms;

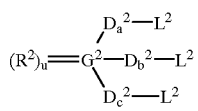
(3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17; $G^2$ represents a nitrogen or phosphorus atom when u is 0 or a phosphorus atom when u is 1, and $R^2$ represents an oxygen or sulfur atom.

2. The catalyst for trimerization of ethylene according to claim 1, wherein the neutral multidentate ligand is facially coordinated in the chromium complex.

3. The catalyst for trimerization of ethylene according to claim 1, which further comprises (d) a radical anion compound.

4. The catalyst for trimerization of ethylene according to claim 1, wherein the alkyl group containing compound is represented by the following formula (4):

$$R_pEX_q \tag{4}$$

wherein p and q are numbers satisfying the formulae: $0<p\leq3$ and $0\leq q<3$, provided that (p+q) is in the range of 1 to 3, E represents lithium, magnesium, zinc, boron or aluminum, each R independently represents an alkyl group having 1 to 10 carbon atoms, and each X independently represents a hydrogen atom, an alkoxide group having 1 to 10 carbon atoms, an aryl group having 6 to 10 carbon atoms or a halogen atom.

5. The catalyst for trimerization of ethylene according to claim 1, which further comprises (c) at least one compound selected from the group consisting of an aromatic tertiary amine compound, except for an imine, and a nitrogen-containing heterocyclic compound.

6. The catalyst for trimerization of ethylene according to claim 5, wherein the neutral multidentate ligand is facially coordinated in the chromium complex.

7. The catalyst for trimerization of ethylene according to claim 3, wherein the radical anion compound is represented by the following formula (5):

$$(Ar)^-_r(M^2)^{r+} \tag{5}$$

wherein Ar is an aromatic hydrocarbon or a heteroatom-containing aromatic hydrocarbon having at least one heteroatom on the aromatic ring, which heteroatom is selected from the group consisting of elements of groups 15 and 16 of the periodic table, wherein said aromatic hydrocarbon and said heteroatom-containing aromatic hydrocarbon may have at least one substituent containing an atom of group 13, 14, 15 or 16 of the periodic table, and two adjacent substituents thereof may form a ring together with the carbon atoms bonded thereto; $M^2$ is a metal selected from the group consisting of an alkali metal and an alkaline earth metal, and r is an integer of 1 when $M^2$ is an alkali metal or an integer of 2 when $M^2$ is an alkaline earth metal.

8. The catalyst for trimerization of ethylene according to claim 5, wherein the alkyl group containing compound is represented by the following formula (4):

$$R_pEX_q \quad (4)$$

wherein p and q are numbers satisfying the formulae: $0<p\leq 3$ and $0\leq q<3$, provided that (p+q) is in the range of 1 to 3, E represents lithium, magnesium, zinc, boron or aluminum, each R independently represents an alkyl group having 1 to 10 carbon atoms, and each X independently represents a hydrogen atom, an alkoxide group having 1 to 10 carbon atoms, an aryl group having 6 to 10 carbon atoms or a halogen atom.

9. The catalyst for trimerization of ethylene according to claim 3, wherein the alkyl group containing compound is represented by the following formula (4):

$$R_pEX_q \quad (4)$$

wherein p and q are numbers satisfying the formulae: $0<p\leq 3$ and $0\leq q<3$, provided that (p+q) is in the range of 1 to 3, E represents lithium, magnesium, zinc, boron or aluminum, each R independently represents an alkyl group having 1 to 10 carbon atoms, and each X independently represents a hydrogen atom, an alkoxide group having 1 to 10 carbon atoms, an aryl group having 6 to 10 carbon atoms or a halogen atom.

10. The catalyst for trimerization of ethylene according to claim 3, wherein the neutral multidentate ligand is facially coordinated in the chromium complex.

11. A process for trimerizing ethylene, comprising:
    trimerizing ethylene in the presence of a catalyst comprising:
    (a) a chromium complex having a neutral multidentate ligand having a tripod structure, represented by the following formula (1):

$$ACrJ_nQ_{3-n} \quad (1)$$

wherein A is a neutral multidentate ligand having a tripod structure, J is a carbonyl ligand or a halogen atom, n is an integer of 0 to 3, and Q is at least one member selected from the group consisting of a hydrogen atom, a hydrocarbon group having 1 to 10 carbon atoms, a carboxylate group having 1 to 10 carbon atoms, a diketonato group having 3 to 10 carbon atoms, an amide group, an imide group, an alkoxide group having 1 to 10 carbon atoms, a thioalkoxide group having 1 to 10 carbon atoms, an arene ligand having 6 to 15 carbon atoms, an alkene ligand having 2 to 10 carbon atoms, an alkene ligand having 2 to 15 carbon atoms, an amine ligand, an imine ligand, a nitrile ligand, an isonitrile ligand, a phosphine ligand, a phosphine oxide ligand, a phosphite ligand, an ether ligand, a sulfide ligand, a sulfone ligand and a sulfoxide ligand, and (b) an alkyl group containing compound;
    said neutral multidentate ligand A in formula (1) being represented by the following formula (2) or formula (3):

(2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms or an aryl group having 6 to 10 carbon atoms;

(3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17; $G^2$ represents a nitrogen or phosphorus atom when u is 0 or a phosphorus atom when u is 1, and $R^2$ represents an oxygen or sulfur atom.

12. A process for trimerizing ethylene according to claim 11, wherein the catalyst further comprises (c) at least one compound selected from the group consisting of aromatic tertiary amine compounds, except for an imine, and nitrogen-containing heterocyclic compounds.

13. A process for trimerizing ethylene according to claim 11, wherein the catalyst further comprises (d) a radical anion compound.

* * * * *